United States Patent
Yaegashi

(10) Patent No.: US 7,819,916 B2
(45) Date of Patent: Oct. 26, 2010

(54) BLOOD PUMP SYSTEM FOR ARTIFICIAL HEART AND APPARATUS SUPERVISORY SYSTEM

(75) Inventor: Mitsutoshi Yaegashi, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 144 days.

(21) Appl. No.: 12/213,083

(22) Filed: Jun. 13, 2008

(65) Prior Publication Data

US 2008/0319544 A1    Dec. 25, 2008

(30) Foreign Application Priority Data

Jun. 20, 2007 (JP) ............................. 2007-162803

(51) Int. Cl.
*A61M 1/10* (2006.01)
(52) U.S. Cl. ............................. 623/3.28; 600/17; 607/48
(58) Field of Classification Search .................. 600/17; 607/48; 348/687; 623/3.18, 3.28
See application file for complete search history.

(56) References Cited

U.S. PATENT DOCUMENTS

| | | | |
|---|---|---|---|
| 5,383,840 A | 1/1995 | Heilman et al. | |
| 6,123,726 A | 9/2000 | Mori et al. | |
| 6,183,412 B1 | 2/2001 | Benkowski et al. | |
| 2002/0116055 A1* | 8/2002 | Snyder | 623/3.18 |
| 2005/0014991 A1 | 1/2005 | Sugiura | |
| 2006/0276855 A1* | 12/2006 | Klapproth et al. | 607/48 |
| 2009/0290069 A1* | 11/2009 | De Vaan et al. | 348/687 |

FOREIGN PATENT DOCUMENTS

JP    2005-434 A    1/2005

* cited by examiner

*Primary Examiner*—Corrine M McDermott
*Assistant Examiner*—Matthew Schall
(74) *Attorney, Agent, or Firm*—Buchanan Ingersoll & Rooney PC

(57) ABSTRACT

A blood pump system for an artificial heart including: a control unit for controlling a blood pump, the control unit including a first alarm generating part for generating a first alarm signal according to the state of the blood pump, and a speaker for outputting an audible sound upon receiving the first alarm signal when the blood pump is in an abnormal state; a supervisory section configured to supervise the state of the control unit; a determining section configured to determine whether the control unit is in an abnormal state or not, based on output signal from the supervisory section; and a second alarm generating part for generating a second alarm signal according to the state of the control unit, based on the result of determination by the determining section.

2 Claims, 7 Drawing Sheets

BLOOD PUMP SYSTEM FOR ARTIFICIAL HEART AND APPARATUS SUPERVISORY SYSTEM

BACKGROUND OF THE INVENTION

The present invention relates to a technology of issuing an alarm according to the state of a controlled apparatus, particularly to an apparatus supervisory system suitable for application to a blood pump system for an artificial heart by which the state of the blood pump and the state of a controller for the blood pump are supervised and an alarm is issued as required.

An artificial heart has hitherto been adopted as an apparatus capable of substituting for the function of a heart. An artificial heart is composed mainly of a blood pump for circulating the blood and a controller for controlling the operation of the blood pump. Upon an abnormal state generated in the operation of the blood pump, the controller functions as alarm generating means for generating an alarm to inform the user of the abnormal state.

Since the blood pump of the artificial heart supports the human life directly, a failure of the alarm generating means may possibly be fatal. In view of this, it has been practiced, as a measure for coping with a failure of the alarm generating means, (1) to confirm the absence of a failure by issuing an alarm sound for confirmation either periodically (in a scheduled manner) or non-periodically (in a nonscheduled manner), and (2) to duplex the alarm generating means.

For example, Japanese Patent Laid-Open No. 2005-434 (corresponding to U.S. Patent No. 2005014991 A1) discloses a technology for informing the user of an abnormal state of a blood pump and an abnormal state of a controller for the blood pump, by use of an LED or a buzzer.

SUMMARY OF THE INVENTION

Meanwhile, the alarm sound for confirmation used in (1) above is an audible sound and, therefore, is offensive to the ear if issued constantly. Therefore, the alarm sound for confirmation has to be issued periodically or in a non-scheduled manner. Thus, the technology for realizing confirmation of the presence/absence of a failure by issuing an alarm sound for confirmation has had a drawback in that there is a time difference (time lag) from the time of failure to the time of confirmation and, hence, it is very difficult to immediately inform that the alarm generating means is in an abnormal state.

On the other hand, the duplexing of the alarm generating means according to (2) above cannot be realized inexpensively and in a small size. The reason is as follows.

FIG. 8 shows the outline of an ordinary blood pump system for an artificial heart according to the related art. The blood pump system for an artificial heart shown in FIG. 8 includes a blood pump 101, a supervisory unit 102 composed of sensors and the like, a decision unit 103 composed of a microcomputer and the like, a speaker driver 104, a speaker 105, and a power supply system 106 for supplying electric power to each component. The operation of the blood pump 101 is supervised by the supervisory unit 102, and supervision data is sent by the supervisory unit 102 to the decision unit 103. The decision unit 103 decides the state of the blood pump 102, based on the supervision data sent from the supervisory unit 102. When the blood pump 101 is in an abnormal state, an alarm signal is supplied from the decision unit 103 to the speaker driver 104, and an alarm sound is outputted from the speaker 105.

In the case (A) where two systems of only the "speaker" are prepared in such a blood pump system for an artificial heart, a failure of the speaker driver 104 and its preceding stage results in that the alarm sound is not outputted, so that the effect of the duplexing cannot be obtained.

In the case (B) where two systems of the "speaker driver+speaker" are prepared, a failure of the decision unit 103 and its preceding stage results in that the alarm sound is not outputted, so that the effect of the duplexing cannot be obtained.

In the case (C) where two systems of the "decision unit+speaker driver+speaker" are prepared, a failure of the supervisory unit 102 results in that the alarm signal or the alarm sound is not outputted, so that the effect of the duplexing cannot be obtained.

In the case (D) where two systems of the "supervisory unit+decision unit+speaker driver+speaker" are prepared, a failure of the power supply system 106 results in that the supervision data, the alarm signal or the alarm sound is not outputted, so that the effect of the duplexing cannot be obtained.

Therefore, in order to perform the duplexing effectively, two systems of the "supervisory unit+decision unit+speaker driver+speaker" and of the power supply system have to be prepared so as to make it possible to cope with a failure of any of these components. This type of duplexing renders the system expensive and large in size, thereby spoiling utility for the user.

Thus, there is a need to realize duplexing of the system alarm with an inexpensive and small-sized configuration through the use of a reduced number of component parts and, further, to make it possible to provoke the user's or medical worker's attention upon a failure of the speaker, the alarm generating means or the like.

According to an embodiment of the present invention, there is provided a system including: a control unit for controlling a controlled apparatus, the control unit including a first alarm generating part for generating a first alarm signal according to the state of the controlled system, and a speaker for outputting an audible sound upon receiving the first alarm signal when the controlled system is in an abnormal state; supervisory means for supervising the state of the control unit; determining means for determining whether the control unit is in an abnormal state or not, based on output signal from the supervisory means; and a second alarm generating part for generating a second alarm signal according to the state of the control unit, based on the result of determination by the determining means.

The controlled apparatus to which this system can be applied suitably is, for example, a blood pump for an artificial heart.

According to the configuration of the just-mentioned system, there are provided two alarm generating functions, i.e., a function to supervise the state of a controlled apparatus such as a blood pump and to generate an alarm and a function to supervise the state of a control unit controlling the controlled apparatus and to generate an alarm.

According to the embodiment of the present invention, duplexing of an alarm can be realized by use of an inexpensive and small-sized configuration. In addition, a configuration may be adopted in which an alarm signal is sent to an external monitor device by use of a radio signal upon a failure of the control unit (alarm generating means), whereby it is possible to arouse the user's or the like person's attention through utilizing the monitor device.

DETAILED DESCRIPTION OF THE PREFERRED EMBODIMENTS

Now, embodiments of the present invention will be described below referring to the accompanying drawings. The embodiments correspond to examples in which the controlled apparatus is a blood pump for an artificial heart, and supervised items as objects of alarming are the blood pump and a controller (control device) for controlling the blood pump which are constituting the blood pump system for an artificial heart.

Figure 1:
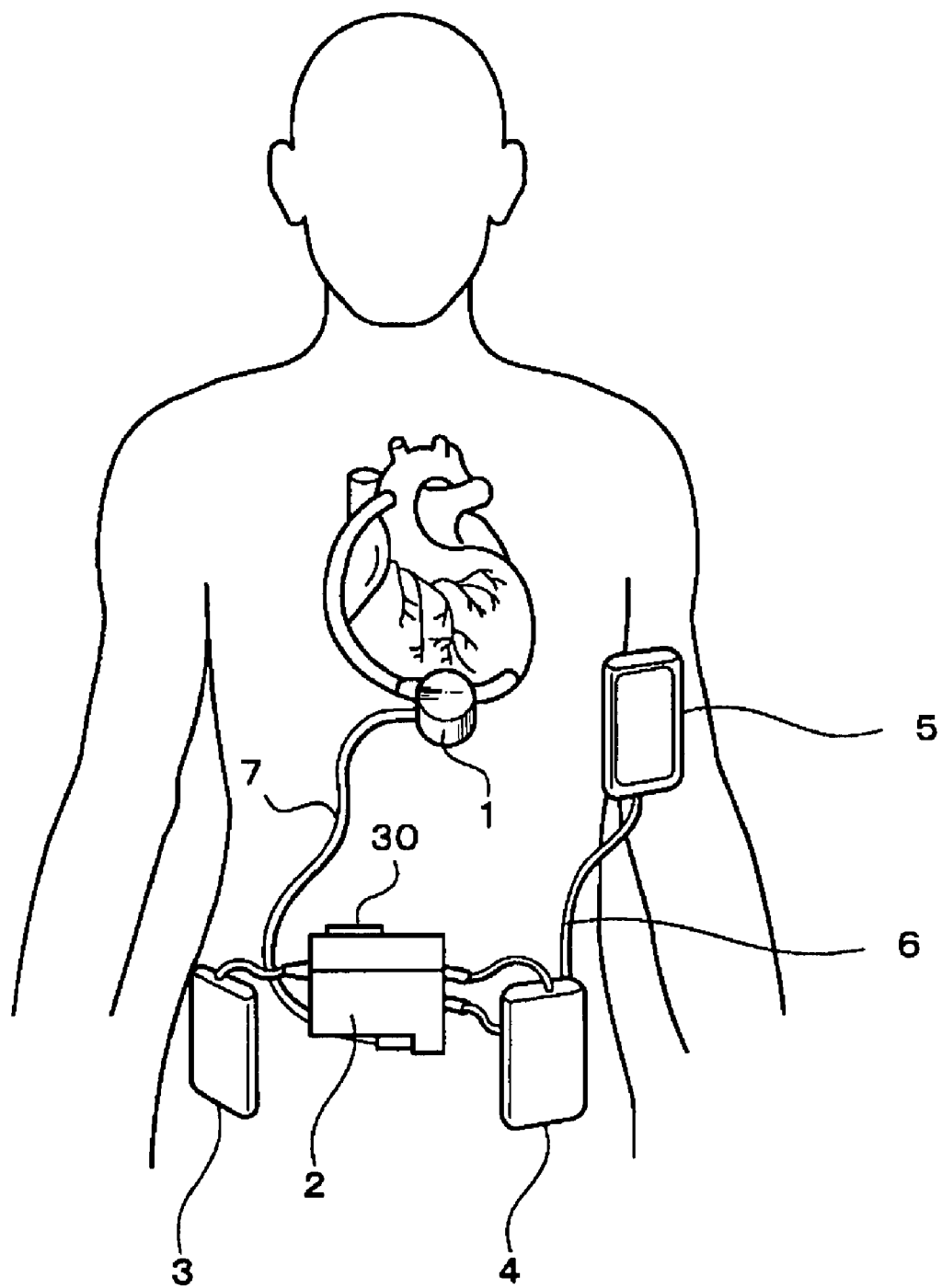
FIG. 1 shows an example of use of a blood pump system for an artificial heart based on the present invention.

FIG. 1 shows a general configuration wherein the blood pump system for an artificial heart is carried by a person. In FIG. 1, the system includes a blood pump 1 embedded in a human body, a controller 2 which is connected to the blood pump 1 through a cable 7 penetrating the skin and which is carried at an extracorporeal part such as a belt part, a detector 30 which is disposed in the controller 2 and which detects an abnormal state, batteries 3 and 4 as a power supply for the controller 2, and a user interface unit 5 for displaying the operating state of the blood pump 1. The blood pump 1 is so disposed that an inflow port of the blood pump 1 is connected to the left ventricle of the heart, and an outflow port is connected to the aorta, whereby a blood bypass line is formed, so as to secure a bloodstream of the patient lowered in the function of the heart.

The user interface unit 5 is connected to the controller 2 through the cable 6, and has a display part which receives signals from the controller 2 and displays the operating state of the blood pump 1, such as the rotating speed of an impeller, blood flow rate, discharge pressure, etc. In addition, the user interface unit 5 also has instruction buttons to be used by the patient (user) or a doctor to, for example, change the settings for the operating conditions of the blood pump system. While the user interface unit 5 is connected to the controller 2 through the cable 6, the connection may be made by use of wireless LAN or the like.

Figure 2:
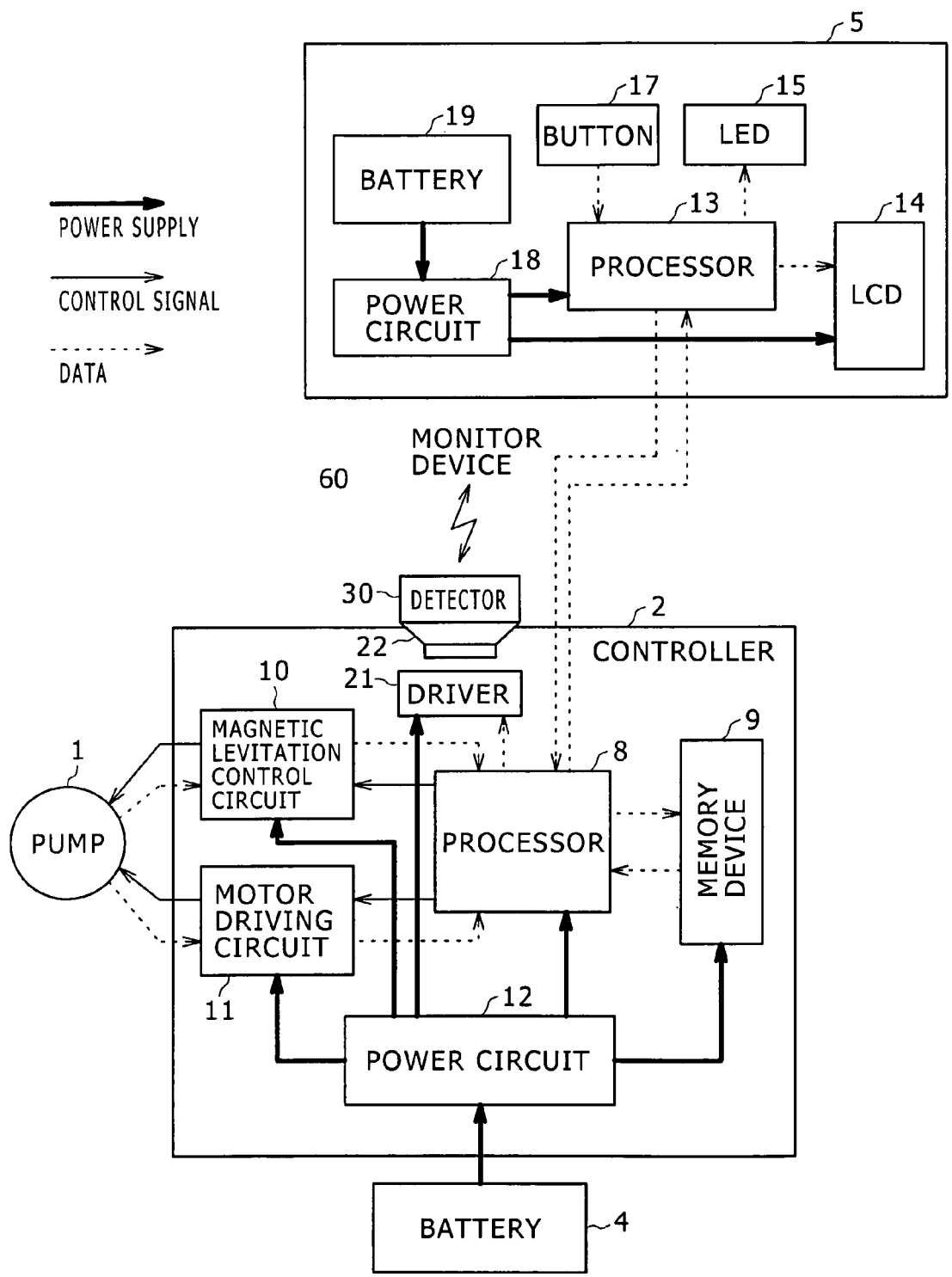
FIG. 2 is a block diagram of the blood pump system for an artificial heart based on the present invention.

FIG. 2 is a block diagram of the blood pump system for an artificial heart. The controller 2 includes a processor 8 for controlling the blood pump 1 and the controller 2 as a whole, a memory device 9 for storing the supervision data of the operating state of the blood pump 1, the operating conditions of the blood pump 1, etc., a magnetic levitation control circuit 10 for magnetically levitate the impeller in the blood pump 1, a motor driving circuit 11 for driving a motor for rotating the impeller, a speaker driver 21 and a speaker 22. Electric power is supplied to each of these components from a power circuit 12.

The speaker driver 21 provided in the controller 2 gets from the processor 8 an alarm signal relating to the operation of the blood pump 1 or to the processor 8 itself, converts the alarm signal from an analog signal to a digital signal, and outputs the digital alarm signal to the speaker 22. Based on the alarm signal inputted from the speaker driver 21, an alarm sound is outputted.

The detector 30 disposed in the controller 2 generates a predetermined alarm signal based on information obtained through the speaker 22 or obtained directly from the controller 2, and sends the alarm signal to the monitor device 60 by radiocommunication. The details of the operation and configuration of the detector 30 will be described later.

On the other hand, the user interface unit 5 connected to the controller 2 through a cable or through wireless LAN or the like includes a user interface processor 13 connected to the processor 8 of the controller 2, a liquid crystal display part (LCD) 14 for displaying the rotating speed of the impeller of the blood pump 1, the blood flow rate, or the discharge pressure, etc., a light emitting diode (LED) 15 for displaying the operating states of the blood pump 1 and the controller 2, instruction buttons 17 by which an instruction to change the operating conditions of the blood pump 1 is given to the processor 13, a power circuit 18 for supplying electric power to the processor 13 and the LCD 14, and a battery 19 as a driving source for the power circuit 18. In FIG. 2, the supply of electric power is indicated by bold solid-line arrows, the flows of control signals are indicated by thin solid-line arrows, and the flows of data are indicated by dotted-line arrows. Incidentally, the user interface unit 5 may be configured integrally in the controller 2.

Now, the embodiments of the blood pump system for an artificial heart according to the present invention will be described in detail below.

First Embodiment

Figure 3:
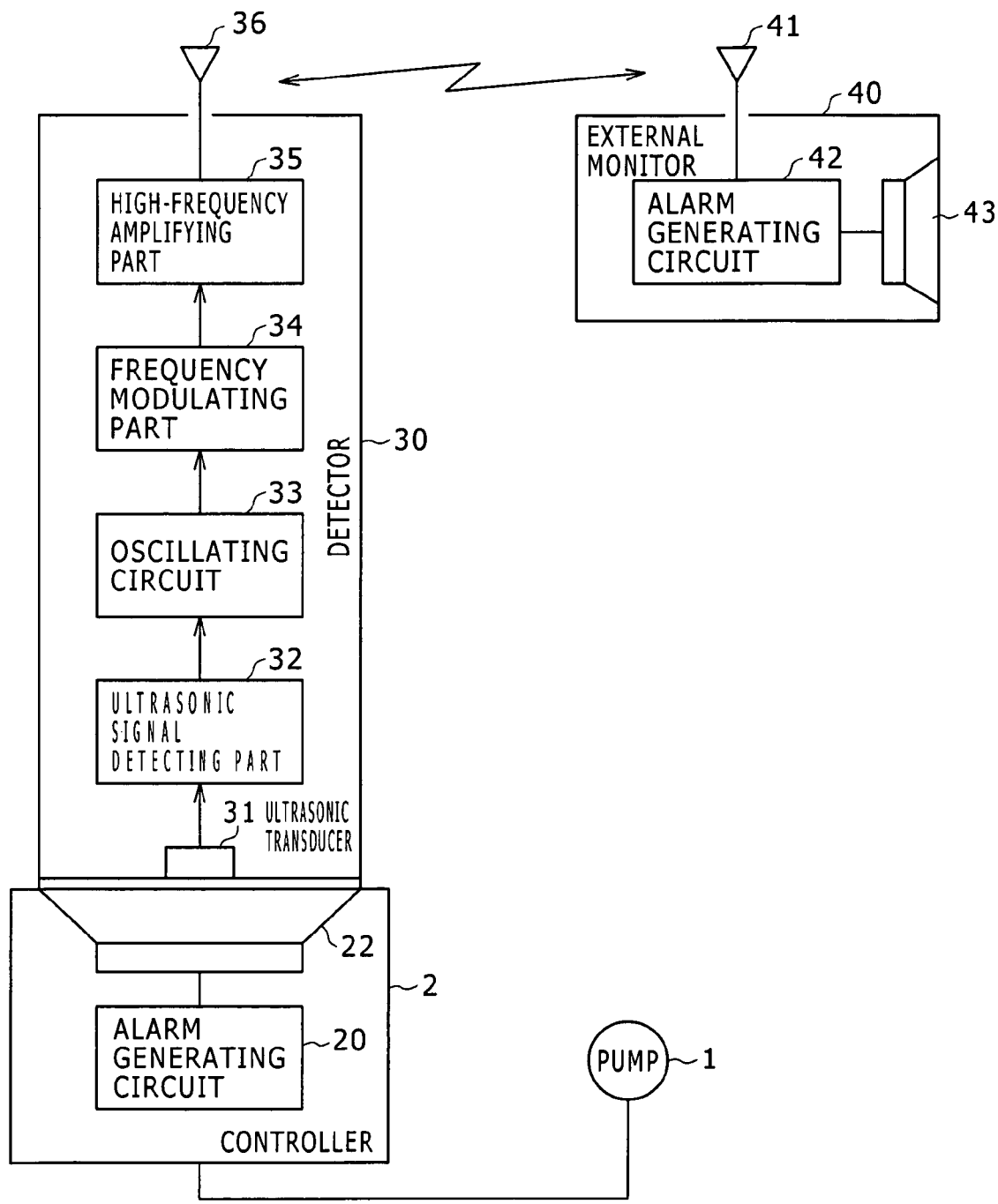
FIG. 3 is a block diagram of the blood pump system for an artificial heart according to a first embodiment of the present invention.

FIG. 3 is a block diagram of the blood pump system for an artificial heart according to a first embodiment. This embodiment corresponds to an example of the blood pump system for an artificial heart in which a detector 30 is mounted to a layout surface of a speaker 22 of a controller 2.

An alarm generating circuit 20 in the controller shown in FIG. 3 is a part (first alarm generating part) obtained by extracting and embodying the function as alarm generating means, which is one of the functions possessed by the processor 8 shown in FIG. 1. The alarm generating circuit 20 sends an alarm signal to the speaker 22 through a speaker driver 21 (omitted in the figure). Incidentally, in FIG. 3, the other parts of the controller 2 shown in FIG. 1 are omitted.

On the other hand, the detector 30 has an ultrasonic transducer 31, an ultrasonic signal detecting part 32, an oscillating circuit 33, a frequency modulating part 34, a high-frequency amplifying part 35 and an antenna 36.

The ultrasonic transducer 31 (ultrasonic wave detecting part) is an example of supervisory means, and functions to detect an ultrasonic signal outputted by the speaker 22 of the controller 2, to convert the ultrasonic signal into an electrical signal, and to output the electrical signal to the ultrasonic signal detecting part 32.

The ultrasonic signal detecting part 32 is an example of determining means, and, based on the electrical signal sent from the ultrasonic transducer 31, functions to determine whether the ultrasonic signal is normal or not, and to output the determination results (a digital signal indicative of whether the ultrasonic signal is normal or not) to the oscillating circuit 33.

The oscillating circuit 33 outputs an oscillation signal when the decision result sent from the ultrasonic signal detecting part 32 is indicating an abnormal state of the ultrasonic signal.

The frequency modulating part 34 modulates the frequency of the oscillation signal outputted from the oscillating circuit 33 into a frequency for radiocommunication, thereby producing a high-frequency signal.

The high-frequency amplifying part 35 amplifies the high-frequency signal outputted from the frequency modulating part 34, and outputs the amplified signal to the antenna 36.

The antenna 36 radiates (sends) the high-frequency signal supplied from the high-frequency amplifying part 35 into space. The radio signal sent from the detector 30 is received by an external monitor 40.

The oscillating circuit 33, the frequency modulating part 34, the high-frequency amplifying part 35 and the antenna 36 constitute an example of the configuration of a second alarm generating part and an output unit.

The external monitor 40 has an antenna 41, an alarm generating circuit 42 and a speaker 43. The alarm generating circuit 42 functions to detect the radio signal received through the antenna 41 and to output an alarm signal to the speaker 43. The external monitor 40 is disposed, for example, in the user's home (room), the patient's room or the like. As the external monitor 40, a commercially available radio set can simply be used. In that case, preliminarily, the external monitor 40 is tuned to the radio frequency of, for example, the FM radio signal of the detector 30, and the power supply of the external monitor 40 is kept ON. Besides, a configuration may be adopted in which, for example, a personal computer with a radiocommunication function connected to a display is utilized as the external monitor 40, and the contents of alarm are displayed on the display, in addition to the output of a sound from the speaker 43.

Now, the operation of the blood pump system for an artificial heart as above will be described. The alarm generating circuit 20 (processor 8) in the controller 2 gets magnetic levitation data from a magnetic levitation control circuit 10, and, based on the data, judges the levitated state of the impeller in the blood pump 1. In addition, the alarm generating circuit 20 gets motor rotation data from the motor driving circuit 11, and, based on the data, judges the rotating state of the motor. Then, the alarm generating circuit 20 decides the presence/absence of an abnormal state in the blood pump 1, based on the magnetic levitation data and the rotation data, and supplies the speaker 22 with a signal according to the decision result.

When an abnormal state needing generation of an alarm such as a failure of the blood pump 1 is present, the alarm generating circuit 20 supplies an audible sound generating signal to the speaker 22 through the speaker driver. On the other hand, during a normal operation, the alarm generating circuit 20 constantly or periodically supplies the speaker 22 with an ultrasonic wave generating signal through the speaker driver. Therefore, the controller 2 causes an audible sound to be outputted from the speaker 22 when an abnormal state needing the generation of alarm is present, and causes an ultrasonic wave signal to be constantly or periodically outputted from the speaker 22.

Upon detecting an abnormal state needing generation of an alarm, the controller 2 causes an audible sound to be outputted from the speaker 22, so that the user can recognize the generation of an abnormal state in the operation of the blood pump 1 or in the operation inside the controller 2. This permits the user to swiftly take an appropriate measure.

On the other hand, during a normal operation of the alarm generating circuit 20 in the controller 2, an ultrasonic signal from the speaker 22 of the controller 2 is detected by the ultrasonic transducer 31, and an electrical signal upon detection is supplied to the ultrasonic signal detecting part 32.

Based on the electrical signal from the ultrasonic transducer 31, the ultrasonic signal detecting part 32 decides whether the ultrasonic signal from the controller 2 is normal or not, and sends the decision result (a digital signal indicative of whether the ultrasonic signal is normal or abnormal) to the oscillating circuit 33. Upon receiving the digital signal indicative of the abnormal state of the ultrasonic signal, the oscillating circuit 33 outputs an oscillation signal.

The condition where the ultrasonic signal is abnormal means, for example, the condition where the ultrasonic signal is not being outputted (sent) from the controller 2, or the condition where the ultrasonic signal is being outputted (sent) but the outputted signal (sent signal) is in an abnormal state.

The oscillation signal outputted from the oscillating circuit 33 is inputted to the frequency modulating part 34, to be modulated into a high-frequency signal. Then, the high-frequency signal outputted from the frequency modulating part 34 is amplified by the high-frequency amplifying part 35, before being sent from the antenna 36 by radio.

Then, the radio signal from the detector 30 is received by the external monitor 40, which generates an alarm.

As has been described above, in the present embodiment, the controller 2 for controlling the blood pump causes an audible-sound alarm to be outputted from the speaker 22 upon an abnormal state needing generation of an alarm. On the other hand, during a normal operation, the controller 2 causes an ultrasonic signal to be outputted from the speaker 22 constantly or periodically. The ultrasonic signal thus outputted from the speaker 22 of the controller 2 is received by the detector 30 disposed to be external to and proximate to the controller 2. Here, in the case where the transmission of the ultrasonic signal is stopped due to a failure of the alarm generating circuit 20 or the speaker 22 or in the case where the ultrasonic signal is in an abnormal state, the detector 30 judges that a failure of the alarm generating circuit 20 or the speaker 22 is present, and sends a radio signal to the external monitor 40, causing the external monitor 40 to issue an alarm.

Therefore, when a failure of the alarm generating circuit 20 or the speaker 22 in the controller 2 is generated, the inputting of the ultrasonic signal from the controller 2 to the detector 30 is stopped, whereon an alarm sound is issued from the speaker 43 of the external monitor 40. Incidentally, in the case where the controller 2 periodically outputs the ultrasonic signal, it is desirable that the alarm sound is issued with a time lag of not more than the time interval of the periodic outputting.

Thus, the blood pump system for an artificial heart according to this embodiment is not based on duplexing of alarm by a method in which the number of component parts is large due to doubling of the same component parts as in the related art. Instead, the blood pump system has the function of generating an alarm while supervising a failure of the alarm generating circuit 20 or the speaker 22 in the controller 2, in addition to the function of generating an alarm while supervising the operation of the blood pump 1. With this system, therefore, duplexing of alarm can be realized.

In the case of the configuration according to this embodiment, the detector 30 can be composed by use of an IC chip, for example. Therefore, the detector 30 can be composed using a small number of component parts, and can be made small in size and weight. Besides, since the detector 30 can be composed by use of a small number of component parts and by use of an IC chip, its power consumption is small, so that it can be driven by a cell such as a button cell.

In addition, referring to FIG. 3, the detector 30 looks like being disposed on the whole surface of the speaker 22 of the controller 30, but, actually, the detector 30 can be reduced in size and, hence, it is sufficiently small as compared to the speaker 22. Therefore, the detector 30 would not obstruct the radiation of the audible sound generated by the speaker 22, so that clear sound reproduction can be achieved.

Besides, in the case where the ultrasonic transducer 31 is separated from the main body of the detector 30 (connection therebetween is made by wiring), it is possible to adhere only the ultrasonic transducer 31 to the layout surface of the speaker 22, so that its influence on the radiation of the audible sound from the speaker 22 is further reduced. In addition, it is possible to enhance the degree of freedom in mounting the detector 30.

Besides, since the detector 30 is small in size and weight, the mounting of the detector 30 to the controller 2 can be made by use of simple means, such as Magic Tape (registered trademark).

Second Embodiment

Figure 4:
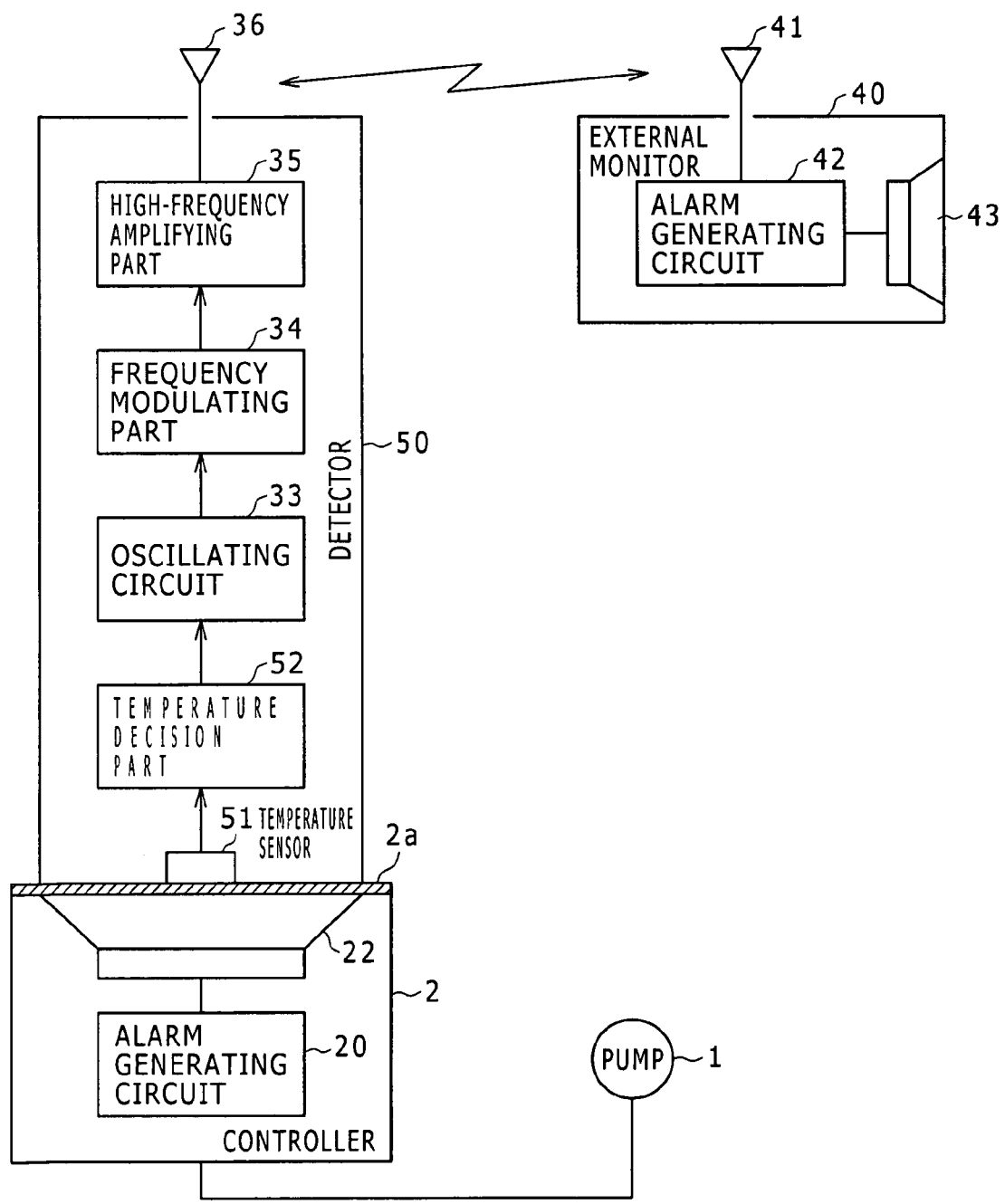
FIG. 4 is a block diagram of the blood pump system for an artificial heart according to a second embodiment of the present invention.

FIG. 4 shows a block diagram of a blood pump system for an artificial heart according to a second embodiment. This embodiment corresponds to an example of the blood pump system for an artificial heart wherein a detector 50 is mounted to a predetermined heat radiating surface of a controller 2. Specifically, the second embodiment differs from the first embodiment (see FIG. 3) in that a temperature sensor is used in place of the ultrasonic transducer as the supervisory means of the detector, and that a temperature decision part is used in place of the ultrasonic signal detecting part as the determining means. In the following description, the parts in FIG. 4 corresponding to the parts in FIG. 3 above will be denoted by the same symbols as used above, and detailed description of the parts will be omitted.

As shown in FIG. 4, the detector 50 is so disposed that the temperature sensor 51 of the detector 50 is placed in contact with a heat radiating surface 2a of the controller 2. Incidentally, while the temperature sensor 51 in the example of FIG. 4 is expressed as making contact with a front surface of the speaker 22, this example is not limitative, since it suffices for the temperature sensor 51 to be mounted to any heat radiating surface of the speaker 22.

The temperature sensor 51 is an example of the supervisory means, and has a function by which the temperature obtained from the heat radiating surface 2a of the controller 2 is converted into an electrical signal having a voltage or current value according to the temperature value, and the electrical signal is outputted to the temperature decision part 52. As the temperature sensor 51, there can be used a thermistor to be used in contact with the heat radiating surface, or a sensor for radiation temperature measurement (thermopile, bolometer, etc.) which can be used out of contact with the heat radiating surface. Incidentally, a configuration may be adopted in which the conversion of an electrical analog signal to a digital signal is conducted on the temperature sensor 51 side and the digital signal is outputted to the temperature decision part 52.

The temperature decision part 52 is an example of the determining means, and has a function by which whether the temperature of the controller 2 is normal or not is determined based on the electrical signal sent from the temperature sensor 51, and the decision result (a digital signal indicative of whether the temperature is normal or not) is outputted to an oscillating circuit 33. A nonvolatile memory such as ROM (not shown) stores a table showing the relation between the temperature of the heat radiating surface 2a of the controller 2 and the magnitude of an electric signal outputted from the temperature sensor 51, and a table showing the range of normal temperatures and the range of abnormal temperature, and the temperature decision part 52 decides whether the temperature of the controller 2 is normal or abnormal by referring to the tables stored in the nonvolatile memory.

Now, the operation of the blood pump system for an artificial heart will be described below. The alarm generating circuit 20 (processor 8) of the controller 2 decides the abnormality of the blood pump 1, based on the magnetic levitation data and the rotation data got from the magnetic levitation control circuit 10 and the motor driving circuit 12, and supplied the speaker 22 a signal according to the decision result.

The alarm generating circuit 20 supplies the speaker 22, through the speaker driver, with a signal which produces an audible sound in response to an abnormal state needing the generation of an alarm, such as a failure of the blood pump 1. Therefore, the controller 2 outputs an audible sound from the speaker 22 upon an abnormal state of the blood pump 1 or the like which needs generation of an alarm. Thus, when an abnormal state needing generation of an alarm is present in the controller 2, the controller 2 outputs the audible sound from the speaker 22, whereby the user is permitted to recognize that an abnormal state is generated in the operation of the blood pump 1 or in the operation inside the controller 2. This enables the user to swiftly take a suitable measure.

On the other hand, the detector 50 constantly or periodically measure the temperature of the heat radiating surface 2a of the controller 2 by the temperature sensor 51, and the detector 50 supplies the temperature decision part 52 with temperature data (electrical signal) on the heat radiating surface 2a of the controller 2 which is obtained through the temperature sensor 51.

The temperature decision part 52 determines whether the temperature of the controller 2 is normal or not, based on the electrical signal from the temperature sensor 51, and sends the determination result (a digital signal indicative of whether the temperature is normal or abnormal) to the oscillating circuit 33. The oscillating circuit 33 outputs an oscillation signal upon receiving a digital signal indicative of the abnormal state of the temperature.

Incidentally, in this embodiment, only such a grave abnormal state as generation of an abnormal temperature in the controller 2 is detected. Therefore, the temperature decision part 52 decides the presence/absence of an abnormal temperature corresponding to stoppage of the blood pump 1 (lowering in heat build-up), transition from magnetic bearing to hydrodynamic bearing (lowering in heat build-up), stoppage of the magnetic levitation control circuit 10 or the motor driving circuit 11 (lowering in heat build-up), an abnormal state of the blood pump 1 or an electronic part (rise in heat build-up) or the like case.

The oscillation signal outputted from the oscillating circuit 33 is inputted to a frequency modulating part 34, which modulates the oscillation signal into a high-frequency signal. Then, the high-frequency signal outputted from the frequency modulating part 34 is amplified by the high-frequency amplifying part 35, before being sent from the antenna 36 by radio.

The radio signal from the detector 30 is received by the external monitor 40, which issues an alarm.

As has been described above, in this embodiment, heat radiation from the controller 2 for the blood pump 1 is supervised by the detector 40 disposed to be external to and proximate to the controller 2, through the use of the temperature sensor 51. The controller 2 for controlling the blood pump 1 outputs, from the speaker 22, an audible sound as an alarm upon an abnormal state needing generation of the alarm. On the other hand, when the temperature of the controller 2 becomes abnormal, the temperature decision part 52 of the detector 40 decides that the situation indicates an abnormal state of the blood pump 1 or of the controller 2 inclusive of the alarm generating circuit 20, and it sends a signal to the external monitor 40 by radio, thereby causing the external monitor 40 to issue an alarm.

Therefore, when the temperature decision part 52 decides that the temperature of the controller 2 is abnormal, not only an audible sound as an alarm is outputted from the speaker 22 of the controller 2 but also an alarm is issued by the external monitor 40 (duplexing of alarm). In short, even if the alarm generating circuit 20 or the speaker 22 in the controller 2 has failed, the detector 50 having sensed the abnormal temperature causes the external monitor 40 to issue an alarm.

Thus, the blood pump system for an artificial heart according to this embodiment does not make duplexing of alarm by a method based on the use of an increased number of component parts, for example, double arrangement of the same component parts as in the related art. Instead, the blood pump system has the function of generating an alarm while supervising the operations of the blood pump 1 and the controller 2 by utilizing temperature data even upon a failure in the alarm generating circuit 20 or the speaker 22, in addition to the function of generating an alarm while supervising the operation of the blood pump 1 during the normal operation of the alarm generating circuit 20. This makes it possible to realize duplexing of alarm.

In the case of the configuration according to this embodiment, the detector 50 can be composed by use of an IC chip, for example. Therefore, the detector 50 can be made small in size and weight. In addition, the power consumption of the detector 50 is small, so that the detector 50 can be driven by a cell such as a button cell.

Besides, in the case where the temperature sensor 51 is separate from the main body of the detector 50 (connection therebetween is made by wiring, for example), it is possible to adhere only the temperature sensor 51 to the heat radiating surface 2a, and hence to enhance the degree of freedom in mounting the detector 50.

In addition, since the detector 50 is small in size and weight, it can be mounted to the controller by use of simple means such as Magic Tape (registered trademark).

This embodiment exhibits not only the above-mentioned actions and effects but also the same actions and effects as those in the case of the first embodiment above.

Furthermore, an embodiment may be adopted in which the mode of generating an alarm based on temperature data on the controller 2 according to the present embodiment and the mode of generating an alarm based on an ultrasonic signal from the controller 2 according to the first embodiment are combined with each other.

Third Embodiment

Figure 5:
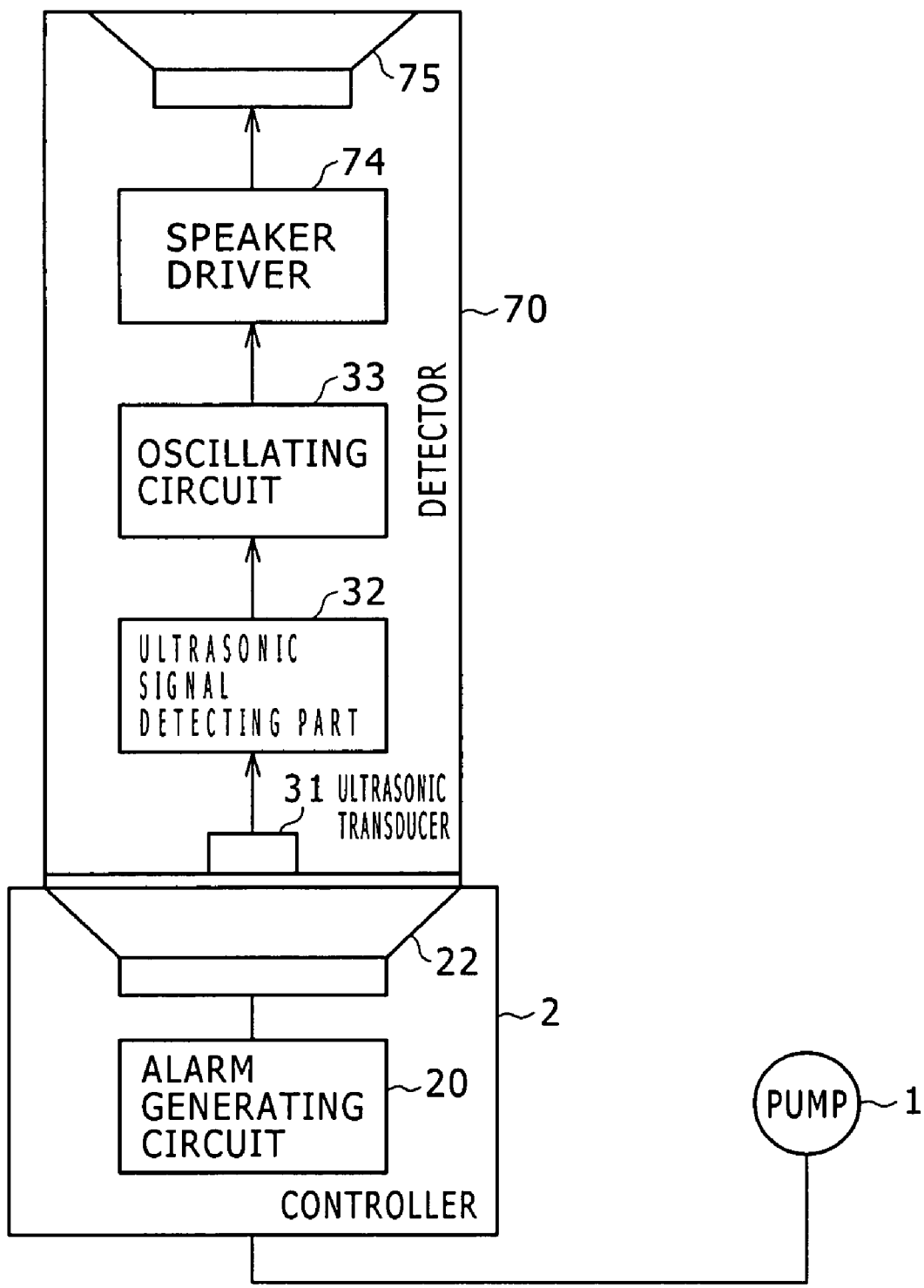
FIG. 5 is a block diagram of the blood pump system for an artificial heart according to a third embodiment of the present invention.

FIG. 5 is a block diagram of a blood pump system for an artificial heart according to a third embodiment. This embodiment corresponds to an example wherein the detector in the blood pump system for an artificial heart in the first embodiment above is provided with an alarm generating function. Specifically, the third embodiment differs from the first embodiment (see FIG. 3) in that, instead of sending a radio signal containing alarm data from the detector to the monitor device, the detector is provided with a speaker driver 74 and a speaker 75 for the purpose of outputting an alarm. In the following description, the parts in FIG. 5 corresponding to the parts in FIG. 3 are denoted by the same symbols as used above, and detailed descriptions of these parts will be omitted.

The operation of a controller 2 is the same as in the first embodiment. Specifically, the controller 2 outputs an audible sound from a speaker 22 when a blood pump 1 is in an abnormal state needing generation of an alarm, and constantly or periodically outputs an ultrasonic signal from the speaker 22 during a normal operation of the blood pump 1. Therefore, when the controller 2 is in an abnormal state needing an alarm, the controller 2 outputs an audible sound from the speaker 22, so that the user can recognize that an abnormal state has been generated in the operations inside the controller 2. This permits the user to speedily take a suitable measure.

On the other hand, during a normal operation of an alarm generating circuit 20 in the controller 2, a detector 70 detects an ultrasonic signal from the speaker 22 of the controller 2 through the function of an ultrasonic transducer 31, and supplies an electrical signal based on the detection to an ultrasonic signal detecting part 32.

Based on the electrical signal from the ultrasonic transducer 31, the ultrasonic signal detecting part 32 determines whether the ultrasonic signal from the controller 2 is normal or not, and sends the determination result (a digital signal indicative of whether the ultrasonic signal is normal or not) to an oscillating circuit 33. The oscillating circuit 33 outputs an oscillation signal upon receiving the digital signal indicating that the ultrasonic signal is abnormal.

The oscillation signal outputted from the oscillating circuit 33 is inputted through the speaker driver 74 to the speaker 75, and an alarm sound is outputted from the speaker 75.

When the alarm generating circuit 20 or the speaker 22 in the controller 2 has failed, the inputting of the ultrasonic signal from the controller 2 to the detector 70 is stopped at the time of failure, and, immediately, an alarm sound is outputted from the speaker 75.

In this embodiment, the oscillating circuit 33, the speaker driver 74 and the speaker 75 function as a second alarm generating part.

Thus, the blood pump system for an artificial heart according to this embodiment does not adopt duplexing of alarm by a method based on the use of an increased number of component parts such as double arrangement of the same component parts as in the related art. Instead, the blood pump system in this embodiment is provided with not only the function of generating an alarm while supervising the operation of the blood pump 1 but also the function of generating an alarm while supervising the presence/absence of a failure of the alarm generating circuit 20 or the speaker 22 of the controller 2.

In the case of the configuration in this embodiment, the detector 70 is greater in size than that in the first embodiment by an amount corresponding to the speaker driver 74 and the speaker 75, but it has the advantage of being able to function effectively even in a place where no external monitor is provided.

Incidentally, in the example shown in FIG. 5, the radiocommunication function (the frequency modulating part 34, the high-frequency amplifying part 35, and the antenna 36) in the first embodiment (see FIG. 3) is omitted from the illustration. In the case where the detector 70 is provided with both the radiocommunication function and the alarming function utilizing the speaker 75, both the detector 70 and the alarm device issue an alarm sound upon a failure of the alarm generating circuit 20 or the speaker 22. In addition, it is possible to reduce the size of the detector 70 in the case where the radiocommunication function is omitted, as shown in FIG. 5.

The present embodiment exhibits not only the just-mentioned actions and effects but also the same actions and effects as those in the first embodiment.

Fourth Embodiment

Figure 6:
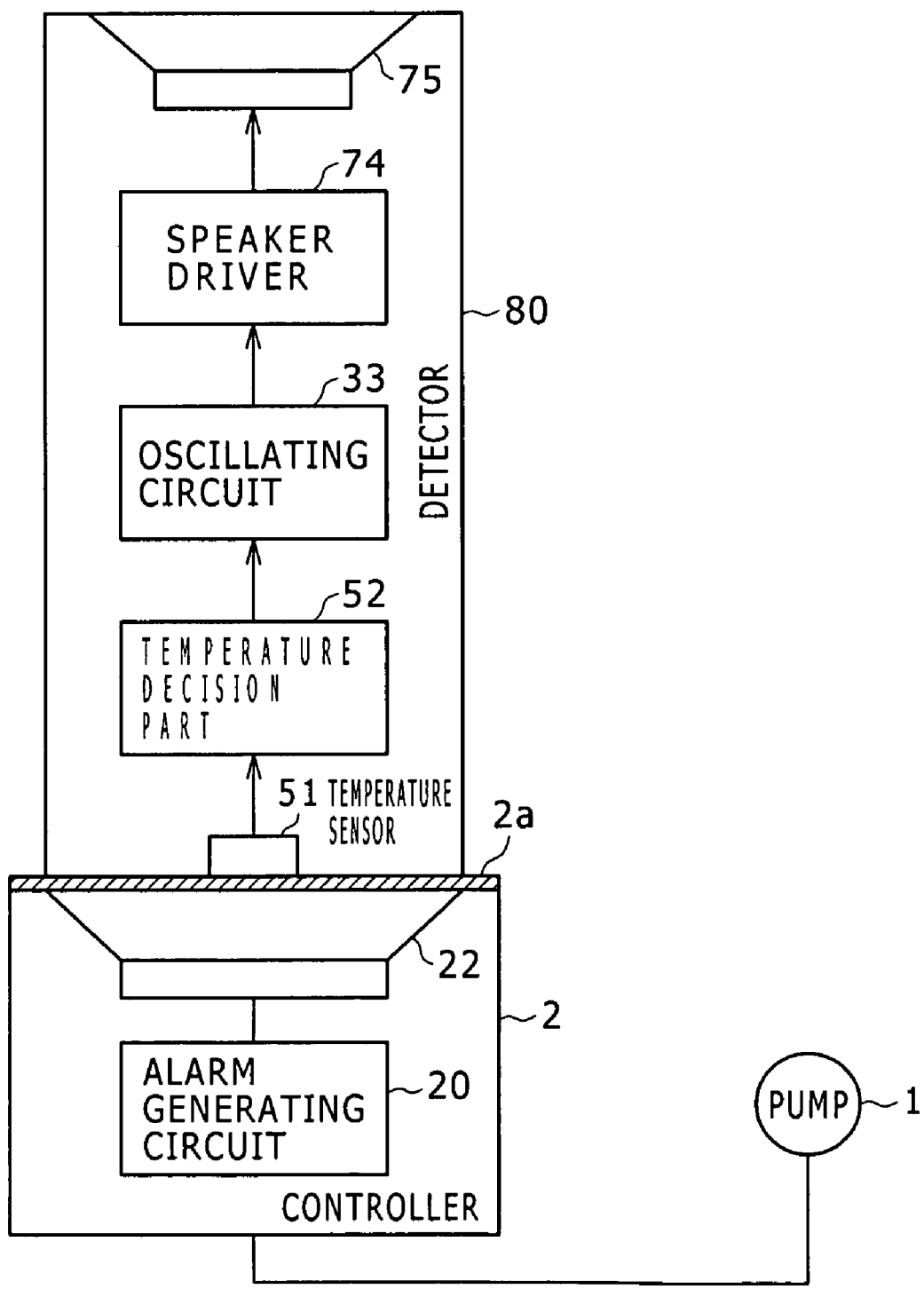
FIG. 6 is a block diagram of the blood pump system for an artificial heart according to a fourth embodiment of the present invention.

FIG. 6 shows a block diagram of a blood pump system for an artificial heart according to a fourth embodiment. This embodiment corresponds to an example wherein the detector in the blood pump system for an artificial heart according to the second embodiment is provided with an alarm generating function. Specifically, the fourth embodiment differs from the second embodiment (see FIG. 4) in that, instead of sending a radio signal containing alarm data from the detector to the monitor device, the detector is provided with a speaker driver 74 and a speaker 75 for outputting an alarm. In the following description, the same parts in FIG. 6 as those in FIG. 4 are denoted by the same symbols as used above, and detailed descriptions of these parts will be omitted.

The operation of a controller 2 is the same as in the first to third embodiments above. Specifically, the controller 2 outputs an audible sound from a speaker 22 when a blood pump 1 is in an abnormal state needing generation of an alarm. Therefore, when the controller 2 is in an abnormal state needing generation of an alarm, the controller 2 outputs an audible sound from the speaker 22, so that the user can recognize that an abnormal state is generated in the operation of the blood pump 1 or in the operations inside the controller 2. This enables the user to speedily take a suitable measure.

On the other hand, a detector 80 supervises whether the temperature of a heat radiating surface 2a of the controller 2 is normal or not while measuring the temperature by a temperature sensor 51 either constantly or periodically. The detector 80 supplies a temperature decision part 52 with temperature data (electrical signal) on the heat radiating surface 2a of the controller 2 obtained through the temperature sensor 51.

Based on the electrical signal from the temperature sensor 51, the temperature decision part 52 determines whether the temperature of the controller 2 is normal or not, and sends the determination result (a digital signal indicative of whether the temperature is normal or abnormal) to an oscillating circuit 33. The oscillating circuit 33 outputs an oscillation signal upon receiving the digital signal indicating that the temperature is abnormal.

The oscillation signal outputted from the oscillating circuit 33 is inputted through the speaker driver 74 to the speaker 75, and an alarm sound is outputted from the speaker 75.

When the blood pump 1 has failed or an abnormal state is generated in the temperature of the controller 2, the temperature sensor 51 of the detector 80 detects the abnormal temperature, and an alarm sound is issued from the speaker 75 immediately upon the generation of the failure or the abnormal temperature.

Thus, the blood pump system for an artificial heart according to this embodiment does not adopt duplexing of alarm by a method base on the use of an increased number of component parts such as double arrangement of the same component parts as in the related art. Instead, the blood pump system in this embodiment is provided with not only the function of generating an alarm while supervising the operation of the blood pump 1 during a normal operation of the alarm generating circuit 20 or the speaker 22 but also the function of generating an alarm while supervising the operations of the blood pump 1 and the controller 2 by utilizing temperature data even when the alarm generating circuit 20 or the speaker 22 has failed. This makes it possible to realize duplexing of alarm.

In the case of the configuration according to this embodiment, the detector 80 is larger in size than that in the second embodiment by an amount corresponding to the speaker driver 74 and the speaker 75, but has a merit of being able to function effectively even in a place where no external monitor is provided.

Incidentally, in the example shown in FIG. 6, the radiocommunication function (the frequency modulating part 34, the high-frequency amplifying part 35, and the antenna 36) in the second embodiment (see FIG. 4) is omitted from the illustration. In the case where the detector 80 is provided with both the radiocommunication function and the alarming function utilizing the speaker 75, both the detector 80 and the alarm device issue an alarm sound when the alarm generating circuit 20 or the speaker 22 has failed. In addition, it is possible to reduce the size of the detector 80 in the case where the radiocommunication function is omitted, as shown in FIG. 6.

The present embodiment exhibits not only the just-mentioned actions and effects but also the same actions and effects as those in the second embodiment above.

Fifth Embodiment

Figure 7:
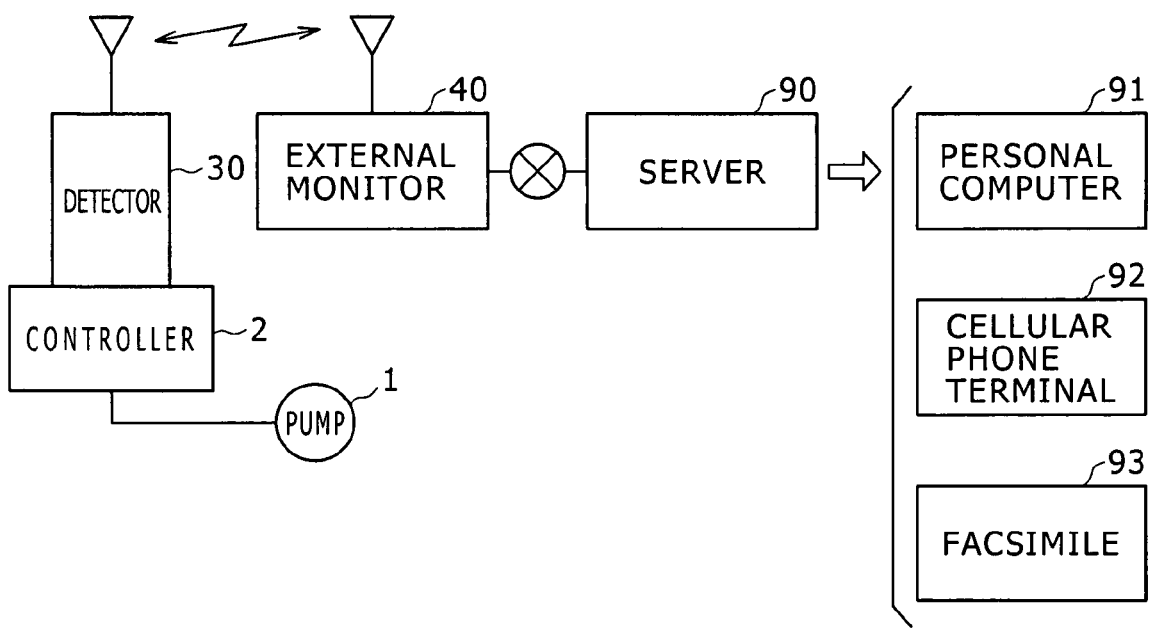
FIG. 7 is a block diagram of the blood pump system for an artificial heart according to a fifth embodiment of the present invention.
Figure 8:
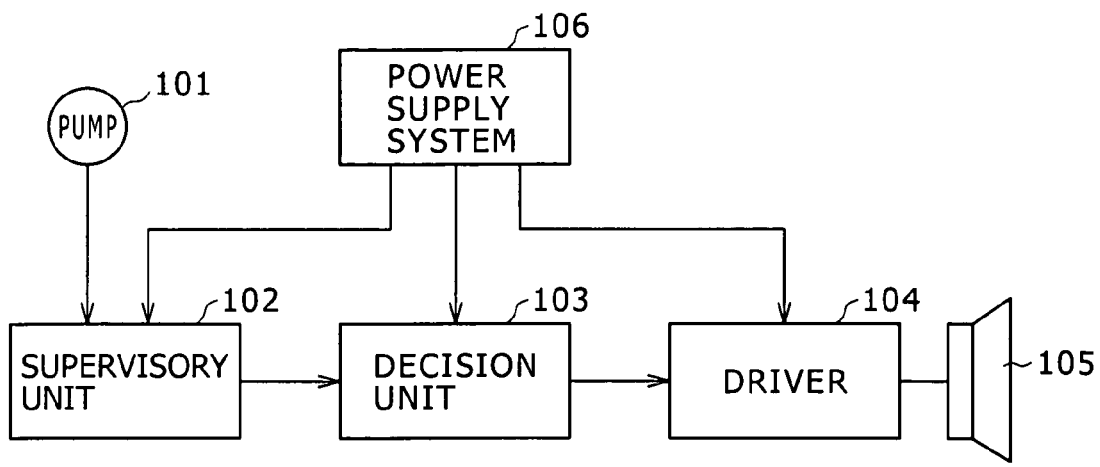
FIG. 8 is a block diagram of a blood pump system for an artificial heart according to the related art.

FIG. 7 shows a block diagram of a blood pump system for an artificial heart according to a fifth embodiment. This embodiment corresponds to an example wherein the detector in the blood pump system for an artificial heart according to the first embodiment is provided with a function of directly informing a medical worker, a nursing person or the like of an abnormal state from a monitor device disposed in the user's home or in the patient's room or the like, through a server connected to a network. In the following description, the parts in FIG. 7 corresponding to those in FIG. 3 are denoted by the same symbols as used above, and detailed descriptions of these parts will be omitted.

In FIG. 7, when an alarm generating circuit 20 or a speaker 22 (see FIG. 3) in a controller 2 has failed, a radio signal (alarm signal) containing the information that the alarm generating circuit 20 or the speaker 22 has failed is sent from a detector 30 to an external monitor 40. The external monitor 40 sends the thus received alarm signal to the server 90 through the network. Then, according to a program and settings recorded in a ROM or the like inside the server 90, the server 90 sends an alarm signal to an electronic apparatus possessed by a predetermined medical worker or the like.

Examples of the communication means (electronic apparatus) for providing the medical worker with the alarm signal include a personal computer 91 installed in a nurse station or the like, a cellular phone terminal 92 (inclusive of electronic mail) possessed by each medical worker, and a facsimile 93 installed in a hospital.

Examples of the network include the internet, a LAN (Local Area Network), and a radiocommunication network.

In addition, a system may be adopted in which the detector 30 is provided with a radiocommunication function such as a cellular phone function, and the detector 30 directly sends an alarm signal to each electronic apparatus by use of the radiocommunication function, instead of through the external monitor 40 and the server 90.

Besides, while this embodiment is an example of application of the first embodiment, this embodiment may also be applied to the second to fourth embodiments, whereby the same effects as above-mentioned can be obtained.

As has been described above, according to the embodiments of the present invention, duplexing of alarm can be realized by use of inexpensive and small-sized configurations, and it is possible to arouse the user's or medical worker's attention upon a failure of an alarm generating circuit or the like.

The present invention is not to be limited to the above-described embodiments, and various modifications and alterations can naturally be made within the scope of the gist of the invention. For example, while an example wherein a controlled system to be controlled by the controller (control unit) is a blood pump for an artificial heart has been described in each of the above embodiments, the invention may be applied to an apparatus supervisory system in which an assistant to other organ or a general electronic apparatus is used as a controlled system, whereby duplexing of alarm can be realized.

What is claimed is:

1. A blood pump system for an artificial heart comprising:
   a blood pump;
   a control unit including a first speaker and a first alarm generating section connected to the pump and to the first speaker for selectively sending a first signal or a second signal to the speaker;
   wherein when said pump is in an abnormal state, the first signal is generated to cause the first speaker to emit an audible sound, and
   wherein when the pump is in a normal state, the second signal is generated to cause the first speaker to emit an ultrasonic wave;
   a detector unit including:
      a detecting section for detecting sonic waves received from the first speaker,
      a determining section connected to the detecting section for determining that the control unit is in an abnormal state when no ultrasonic waves are outputted from the first speaker, or when an ultrasonic wave outputted from the first speaker is in an abnormal state, and
      a second alarm generating section connected to the determining section for emitting a radio signal when the determining section determines that the control unit is in an abnormal state; and
   a monitor device for receiving the radio signal and including a second speaker for converting the radio signal into an audible sound.

2. The blood pump system for an artificial heart according to claim 1, wherein the detector part is removably mounted to the control unit.

* * * * *